(12) United States Patent
Karpishin et al.

(10) Patent No.: US 11,885,797 B2
(45) Date of Patent: *Jan. 30, 2024

(54) IMMUNOFLUORESCENCE ASSAYS

(71) Applicant: Vector Laboratories, Inc., Burlingame, CA (US)

(72) Inventors: Timothy B. Karpishin, Burlingame, CA (US); Pamela James, Redwood City, CA (US); Erika Leonard, San Leandro, CA (US)

(73) Assignee: VECTOR LABORATORIES, INC., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/222,599

(22) Filed: Apr. 5, 2021

(65) Prior Publication Data
US 2022/0057386 A1 Feb. 24, 2022

Related U.S. Application Data

(63) Continuation of application No. 15/970,100, filed on May 3, 2018, now Pat. No. 10,969,384.

(60) Provisional application No. 62/501,439, filed on May 4, 2017.

(51) Int. Cl.
| | | |
|---|---|---|
| G01N 33/542 | (2006.01) | |
| G01N 33/58 | (2006.01) | |
| G01N 33/543 | (2006.01) | |

(52) U.S. Cl.
CPC ..... *G01N 33/542* (2013.01); *G01N 33/54393* (2013.01); *G01N 33/582* (2013.01)

(58) Field of Classification Search
CPC .......... G01N 33/542; G01N 33/54393; G01N 33/582; G01N 33/84
See application file for complete search history.

(56) References Cited

U.S. PATENT DOCUMENTS

| | | |
|---|---|---|
| 4,244,741 A | 1/1981 | Kruse |
| 8,391,955 B2 | 3/2013 | Efimov et al. |
| 10,969,384 B2 * | 4/2021 | Karpishin ............. G01N 33/84 |
| 2009/0233321 A1 | 9/2009 | Verma |
| 2016/0110870 A1 | 4/2016 | Moriyama et al. |
| 2016/0334419 A1 | 11/2016 | Block et al. |

OTHER PUBLICATIONS

Baginski et al., "Review of Phosphate Methodologies," Annals Clin. Lab. Sci., 1975, vol. 5. No. 5, pp. 399-416.*
Fischer et al., "Hematoxylin and Esoin Staining of Tissue and Cell Sections", *Cold Spring Harb. Protoc.*, pp. 1-3, 2008.
Lev et al., "On the use of eosin as a fluorescent dye to demonstrate mucous cells and other structures in tissue sections", *Histochemie*, 20: 363-377, 1969.
PCT/US2018/030799, "International Search Report and Written Opinion", dated Aug. 30, 2018, 13 pages.
Seki, "An evaluation of the P-T (phosphor molybdic acid and tin chloride) method for staining the general structure of central nervous tissues", *Okajimas Folia Anat. Jpn.*, 58(4-6): 987-996, 1982.
Wagrowska-Danilewicz et al., "Immunofluorescent evaluation of renal biopsy: current point of view", *Pol. J. Pathol.*, 61(2): 83-88, 2010.
Brotchie, D. et al., "Localisation of connective tissue and inhibition of autofluorescence in the human optic nerve and nerve head using a modified picrosirius red technique and confocal microscopy", *Journal of Neuroscience Methods*, 8(1), 77-85, 1999.
Davis, A.S. et al., "Characterizing and Dminishing Autoflurescence in Formalin-Fixed Paraffin-embedded Human Respiratory Tissue" *J. Histochem. Cytochem.*, v. 62(6), pp. 405-23, 2014.
Everett, M.M., et al., "The role of phosphotungstic and phosphomolybdic acids in connective tissue staining I. Histochemical studies", *Histochemical Journal*, 6, 25-34, 1974.
Ibrahim, S. et al., "Characterization of glycidyl methacrylate— Crosslinked hyaluronan hydrogel scaffolds incorporating elastogenic hyaluronan oligomers", *Acta Biomaterials*, 7(2), 653-665, 2011.
Nagul, E.A. et al., "The molybdenum blue reaction for the determination of orthophosphate revisited: Opening the black box", *Analytica Chimica Acta*, 890, 60-82, 2015.
Schnell, S.A. et al., "Reduction of Lipofuscin-like Autofluorescence in Fluorescently Labeled Tissue", *The Journal of Histochemistry& Cytochemistry*, 47(6): 719-730, 1999.
Taniguchi, T. et al., "Silica Gel Promotes Reductions of Aldehydes and Ketones by N- Heterocyclic Carbene Boranes", *Organic Letters*, 14(17), 4540-4543, 2012. DOI: 10.1021/oI302010f.

* cited by examiner

*Primary Examiner* — Galina M. Yakovleva
(74) *Attorney, Agent, or Firm* — Norton Rose Fulbright US LLP

(57) ABSTRACT

Provided herein are immunofluorescence assays that do not use an intensely colored lipophilic dye, and that result in a significant reduction of fluorescence due to aldehyde fixation, collagen, elastin, and/or red blood cells. In certain embodiments of the present invention, a two-step treatment of the tissue is contemplated that leads to the incorporation of reduced heteropoly acids or salts thereof (e.g., phosphomolybdate species) in the tissue. This reagent binds tightly to hydrophilic regions of the tissue and effectively quenches the fluorescence in those regions. In doing so, the overall signal-to-noise ratio for the immunofluorescence assay is increased.

14 Claims, 1 Drawing Sheet

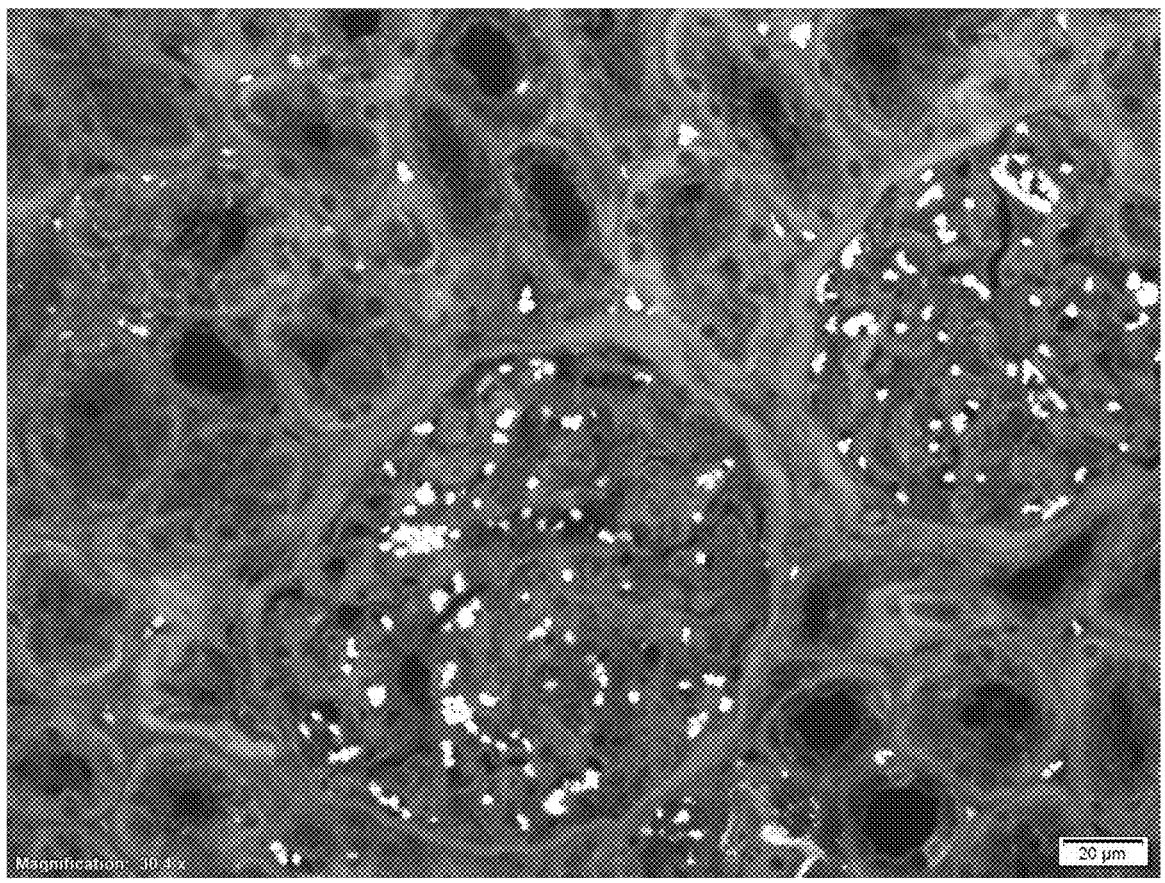

IMMUNOFLUORESCENCE ASSAYS

CROSS-REFERENCE TO RELATED APPLICATIONS

The present invention claims the benefit of priority of U.S. Non-Provisional application Ser. No. 15/970,100 filed May 3, 2018, which claims priority to 62/501,439, filed May 4, 2017, which are hereby incorporated by reference as though set forth herein in its entireties.

FIELD

The present invention relates to immunofluorescence assays and methods for treating samples so as to lower/reduce/mask/suppress the occurrence of background fluorescence in such assays. In certain aspects, the invention relates to immunofluorescence assays and methods for treating samples so as to lower the occurrence of background fluorescence in such assays. In certain aspects, the invention relates to immunofluorescence assays and methods for treating samples so as to reduce the occurrence of background fluorescence in such assays. In certain aspects, the invention relates to immunofluorescence assays and methods for treating samples so as to mask the occurrence of background fluorescence in such assays. In certain aspects, the invention relates to immunofluorescence assays and methods for treating samples so as to suppress the occurrence of background fluorescence in such assays. In certain aspects, the invention relates to kits which facilitate carrying out the invention assays. In certain aspects, the present invention relates to reagents which facilitate carrying out the invention assays (i.e., autofluorescence quenching agents).

BACKGROUND

Immunofluorescence is a technique where a fluorescence microscope is used to visualize targets of interest in a biological section that is affixed to a microscope slide. This technique uses the specificity of fluorescently labeled antibodies or probes that bind to specific targets within a cell, and therefore allows for the examination of the distribution of the target molecules through the tissue sample. Immunofluorescence is widely used in biological and medical sciences.

Fluorescence detection in tissue samples can often, however, be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background.

There are products on the market that attempt to remedy the problem, e.g., (1) Sigma/EMD Millipore offers a product referred to as Autofluorescence Eliminator; (2) Biotium offers a product called TrueBlack Lipofuscin Autofluorescence Quencher; and (3) MaxVision Biosciences offers a product called MaxBlock Autofluorescence Reducing Reagent Kit.

Each of these products uses a similar approach in efforts to lower tissue fluorescence. A very intense black dye (Sudan Black, or comparable dark chromophore) is applied to the tissue, which masks the fluorescent material in the tissue by binding non-specifically to lipophilic regions. By absorbing incident radiation, the dye essentially acts as a filter to reduce the bright signals due to the autofluorescent tissue components. However, this reduction in fluorescence only occurs where the dark chromophore binds, which is lipophilic sections of the tissue. Thus, these products are targeted specifically to the lowering of fluorescence due to lipofuscin, which is observed in some types of tissue.

These and other limitations of state of the art immunofluorescence assays and reagents employed for such assays are hereby addressed by the present invention.

SUMMARY

In accordance with certain embodiments of the present invention, there are provided immunofluorescence assays that do not use an intensely colored lipophilic dye, and that result in a significant reduction of fluorescence due to such causes as aldehyde fixation, collagen, elastin, red blood cells, or the like.

In certain embodiments of the present invention, a two-step treatment of the tissue is contemplated, leading to the incorporation of reduced heteropoly acid(s) or salt(s) thereof, (e.g., phosphomolybdate species) in the tissue. This family of reagents binds tightly to hydrophilic regions of the tissue and effectively quenches the fluorescence in those regions. In doing so, the overall signal-to-noise ratio for the immunofluorescence assay is increased.

The methods described herein can be used to advantage in a variety of applications, i.e., with general fluorescence microscopes, confocal laser microscopes, and the like.

In accordance with additional embodiments of the present invention, there are provided kits which facilitate carrying out the invention assays.

In accordance with certain additional aspects of the present invention, there are also provided reagents which facilitate carrying out the invention assays (i.e., autofluorescence quenching agents).

In accordance with the present invention, the limitations of state of the art immunofluorescence assays have been overcome and the excellent performance of these compounds, formulations, and methods for preparing and using same, have been demonstrated.

BRIEF DESCRIPTION OF THE FIGURE

FIG. 1 illustrates the occurrence of background fluorescence by a kidney tissue section prepared as described in Example 1 at 30× magnification upon 2 second exposure.

DETAILED DESCRIPTION

In accordance with certain embodiments of the present invention, there are provided methods for lowering/reducing/masking/suppressing the occurrence of tissue autofluorescence in an immunofluorescence assay, said methods comprising, before, during or after conducting said immunofluorescence assay:

applying a heteropoly acid or salt thereof, to said tissue, and converting at least a portion of said heteropoly acid or salt thereof into a reduced form.

As used herein, the term "lowering/reducing/masking/suppressing" embraces the many ways in which invention methods improve the signal-to-noise ratio for an immunofluorescence assay, i.e., by lowering the amount of autofluorescence that occurs in an immunofluorescence assay; reducing the amount of autofluorescence that occurs in an immunofluorescence assay; masking the autofluorescence that occurs in an immunofluorescence assay; and/or suppressing the amount of tissue autofluorescence that occurs in an immunofluorescence assay.

In accordance with certain embodiments of the present invention, heteropoly acids or salts thereof are applied to said tissue before conducting said immunofluorescence assay. In such embodiments, the heteropoly acids or salts thereof are subsequently reduced. Alternatively, in accordance with certain embodiments of the present invention, heteropoly acids or salts thereof are applied to said tissue in reduced form.

In accordance with certain embodiments of the present invention heteropoly acids or salts thereof are applied to said tissue while conducting said immunofluorescence assay. In such embodiments the heteropoly acids or salts thereof are subsequently reduced. Alternatively, in accordance with certain embodiments of the present invention, the heteropoly acids or salts thereof are applied to said tissue in reduced form.

In accordance with certain embodiments of the present invention, the heteropoly acids or salts thereof are applied to said tissue after conducting said immunofluorescence assay. In such embodiments, the heteropoly acids or salts thereof are subsequently reduced. Alternatively, the heteropoly acids or salts thereof are applied to the tissue in reduced form.

As readily recognized by those of skill in the art, a wide variety of tissues can be treated according to the invention methods, e.g., tissue obtained from one or more of the lungs, liver, heart, nervous system (including the brain), skin, lymph glands, musculoskeletal system (e.g. bones, joints, muscles), spleen, eyes, sinuses, nasal mucosa, larynx, the gastrointestinal tract, reproductive organs, breast, prostate, salivary glands, tonsils, kidneys, and the like.

Heteropoly acids or salts thereof contemplated for use herein include compounds comprising:
 a metal selected from tungsten, molybdenum or vanadium;
 oxygen;
 an element selected from:
  the p-block of the Periodic Table (e.g., phosphorus, boron, silicon, germanium, tin, arsenic, or antimony),
  the d-block of the Periodic Table (e.g., copper, nickel, cobalt, iron, and chromium), or from
  the Lanthanide series, e.g., cerium, or
  the Actinide series, e.g., thorium, or
  a mixture of any two or more thereof; and
 acidic hydrogen atoms (or one or more cations for a heteropoly anion).

Exemplary heteropoly acids or salts thereof contemplated for use herein have the general formula:

$$H_n A_b D_c O_y \cdot x H_2 O,$$

wherein:
 A is phosphorus, boron, silicon, germanium, tin, arsenic, antimony, copper, nickel, cobalt, iron, cerium, thorium, chromium, or a mixture of any two or more thereof;
 D is molybdenum, tungsten, vanadium, or a mixture of any two or more thereof;
 n is the number of acidic hydrogens in the heteropoly acid (or salt thereof), and is greater than 1, typically falling in the range of 2-10;
 b is 0.1-10 (in some embodiments, b is 0.5-5; in some embodiments, b is 0.5-2.5; in some embodiments, b is 1);
 c is 6-18 (in some embodiments, c is 9-15; in some embodiments, c is 10-12; in some embodiments, c is 12);
 x is the number of moles of water of crystallization (and typically falls in the range of 0-40); and
 y is the number of oxygens in the heteropoly acid (and typically falls in the range of about 10-70).

Exemplary heteropoly anions contemplated for use herein have the general formula:

$$[A_b D_c O_y]^{z-}$$

wherein:
 A is phosphorus, boron, silicon, germanium, tin, arsenic, antimony, copper, nickel, cobalt, iron, cerium, thorium, chromium, or a mixture of any two or more thereof;
 D is molybdenum, tungsten, vanadium, or a mixture of any two or more thereof;
 z is greater than 1, and is the total negative charge on the heteropoly anion;
 b is 0.1-10 (in some embodiments, b is 0.5-5; in some embodiments, b is 0.5-2.5; in some embodiments, b is 1);
 c is 6-18 (in some embodiments, c is 9-15; in some embodiments, c is 10-12; in some embodiments, c is 12); and
 y represents the number of oxygens in the heteropoly anion (and typically falls in the range of 10-70).

As readily recognized by those of skill in the art, a variety of counterions can be associated with the heteropoly anion, e.g., monovalent metal ions such as $Na^+$, $K^+$, $Li^+$, and the like; divalent metal ions such as $Ni^{2+}$, $Co^{2+}$, $Cu^{2+}$, $Zn^{2+}$, and the like; trivalent metal ions such as $Fe^{3+}$, and the like; quaternary ammonium cations (e.g., $NH_4^+$, tetramethyl ammonium, tetrabutyl ammonium, and the like); quaternary phosphonium cations; and the like.

Specific heteropoly acids contemplated for use herein include:
 phosphomolybdic acid (A=phosphorus, D=molybdenum, n=3, b=1, c=12, y=40, and x=0-40),
 phosphotungstic acid acid (A=phosphorus, D=tungsten, n=3, b=1, c=12, y=40, and x=0-40),
 silicomolybdic acid (A=silicon, D=molybdenum, n=4, b=1, c=12, y=40, and x=0-40),
 silicotungstic acid (A=silicon, D=tungsten, n=4, b=1, c=12, y=40, and x=0-40), or
 a mixture of any two or more thereof.

In accordance with certain embodiments of the present invention, the heteropoly acid or salt thereof is applied to said tissue as a solution. In certain embodiments of the present invention, the heteropoly acid or heteropoly anion is applied to tissue as a solution in a range of concentrations from 0.002% (w/v) up to a saturated solution; in certain embodiments, the concentration of heteropoly acid (or heteropoly anion) applied to tissue falls in the range of 0.0025% (w/v) up to a saturated solution; in certain embodiments, the concentration of heteropoly acid (or heteropoly anion) applied to tissue falls in the range of 0.005% (w/v) up to a saturated solution; in certain embodiments, the concentration of heteropoly acid (or heteropoly anion) applied to tissue falls in the range of 0.01% (w/v) up to a saturated solution; in certain embodiments, the concentration of heteropoly acid (or heteropoly anion) applied to tissue falls in the range of 0.1% (w/v) up to a saturated solution; in certain embodiments, the concentration of heteropoly acid (or heteropoly anion) applied to tissue falls in the range of 1.0% (w/v) up to a saturated solution.

In certain embodiments of the present invention, the heteropoly acid or heteropoly anion is applied to tissue as a solution in a range of concentrations from 0.002% (w/v) up to 70% (w/v); in certain embodiments, the concentration of heteropoly acid (or heteropoly anion) applied to tissue falls in the range of 0.002% (w/v) up to 60% (w/v); in certain embodiments, the concentration of heteropoly acid (or heteropoly anion) applied to tissue falls in the range of 0.002% (w/v) up to 50% (w/v); in certain embodiments, the concentration of heteropoly acid (or heteropoly anion) applied to tissue falls in the range of 0.002% (w/v) up to 40% (w/v); in certain embodiments, the concentration of heteropoly acid (or heteropoly anion) applied to tissue falls in the range of 0.002% (w/v) up to 30% (w/v); in certain embodiments, the concentration of heteropoly acid (or heteropoly anion) applied to tissue falls in the range of 0.002% (w/v) up to 20% (w/v); in certain embodiments, the concentration of heteropoly acid (or heteropoly anion) applied to tissue falls in the range of 0.002% (w/v) up to 10% (w/v).

In certain embodiments of the present invention, the heteropoly acid or heteropoly anion is applied to tissue as a solution in a range of concentrations from 0.0025% (w/v) up to 70% (w/v); in certain embodiments, the concentration of heteropoly acid (or heteropoly anion) applied to tissue falls in the range of 0.0025% (w/v) up to 60% (w/v); in certain embodiments, the concentration of heteropoly acid (or heteropoly anion) applied to tissue falls in the range of 0.0025% (w/v) up to 50% (w/v); in certain embodiments, the concentration of heteropoly acid (or heteropoly anion) applied to tissue falls in the range of 0.0025% (w/v) up to 40% (w/v); in certain embodiments, the concentration of heteropoly acid (or heteropoly anion) applied to tissue falls in the range of 0.0025% (w/v) up to 30% (w/v); in certain embodiments, the concentration of heteropoly acid (or heteropoly anion) applied to tissue falls in the range of 0.0025% (w/v) up to 20% (w/v); in certain embodiments, the concentration of heteropoly acid (or heteropoly anion) applied to tissue falls in the range of 0.0025% (w/v) up to 10% (w/v).

In certain embodiments of the present invention, the heteropoly acid or heteropoly anion is applied to tissue as a solution in a range of concentrations from 0.005% (w/v) up to 70% (w/v); in certain embodiments, the concentration of heteropoly acid (or heteropoly anion) applied to tissue falls in the range of 0.005% (w/v) up to 60% (w/v); in certain embodiments, the concentration of heteropoly acid (or heteropoly anion) applied to tissue falls in the range of 0.005% (w/v) up to 50% (w/v); in certain embodiments, the concentration of heteropoly acid (or heteropoly anion) applied to tissue falls in the range of 0.005% (w/v) up to 40% (w/v); in certain embodiments, the concentration of heteropoly acid (or heteropoly anion) applied to tissue falls in the range of 0.005% (w/v) up to 30% (w/v); in certain embodiments, the concentration of heteropoly acid (or heteropoly anion) applied to tissue falls in the range of 0.005% (w/v) up to 20% (w/v); in certain embodiments, the concentration of heteropoly acid (or heteropoly anion) applied to tissue falls in the range of 0.005% (w/v) up to 10% (w/v).

In certain embodiments of the present invention, the heteropoly acid or heteropoly anion is applied to tissue as a solution in a range of concentrations from 0.01% (w/v) up to 70% (w/v); in certain embodiments, the concentration of heteropoly acid (or heteropoly anion) applied to tissue falls in the range of 0.01% (w/v) up to 60% (w/v); in certain embodiments, the concentration of heteropoly acid (or heteropoly anion) applied to tissue falls in the range of 0.01% (w/v) up to 50% (w/v); in certain embodiments, the concentration of heteropoly acid (or heteropoly anion) applied to tissue falls in the range of 0.01% (w/v) up to 40% (w/v); in certain embodiments, the concentration of heteropoly acid (or heteropoly anion) applied to tissue falls in the range of 0.01% (w/v) up to 30% (w/v); in certain embodiments, the concentration of heteropoly acid (or heteropoly anion) applied to tissue falls in the range of 0.01% (w/v) up to 20% (w/v); in certain embodiments, the concentration of heteropoly acid (or heteropoly anion) applied to tissue falls in the range of 0.01% (w/v) up to 10% (w/v).

In certain embodiments of the present invention, the heteropoly acid or heteropoly anion is applied to tissue as a solution in a range of concentrations from 0.1% (w/v) up to 70% (w/v); in certain embodiments, the concentration of heteropoly acid (or heteropoly anion) applied to tissue falls in the range of 0.1% (w/v) up to 60% (w/v); in certain embodiments, the concentration of heteropoly acid (or heteropoly anion) applied to tissue falls in the range of 0.1% (w/v) up to 50% (w/v); in certain embodiments, the concentration of heteropoly acid (or heteropoly anion) applied to tissue falls in the range of 0.1% (w/v) up to 40% (w/v); in certain embodiments, the concentration of heteropoly acid (or heteropoly anion) applied to tissue falls in the range of 0.1% (w/v) up to 30% (w/v); in certain embodiments, the concentration of heteropoly acid (or heteropoly anion) applied to tissue falls in the range of 0.1% (w/v) up to 20% (w/v); in certain embodiments, the concentration of heteropoly acid (or heteropoly anion) applied to tissue falls in the range of 0.1% (w/v) up to 10% (w/v).

In certain embodiments of the present invention, the heteropoly acid or heteropoly anion is applied to tissue as a solution in a range of concentrations from 1.0% (w/v) up to 70% (w/v); in certain embodiments, the concentration of heteropoly acid (or heteropoly anion) applied to tissue falls in the range of 1.0% (w/v) up to 60% (w/v); in certain embodiments, the concentration of heteropoly acid (or heteropoly anion) applied to tissue falls in the range of 1.0% (w/v) up to 50% (w/v); in certain embodiments, the concentration of heteropoly acid (or heteropoly anion) applied to tissue falls in the range of 1.0% (w/v) up to 40% (w/v); in certain embodiments, the concentration of heteropoly acid (or heteropoly anion) applied to tissue falls in the range of 1.0% (w/v) up to 30% (w/v); in certain embodiments, the concentration of heteropoly acid (or heteropoly anion) applied to tissue falls in the range of 1.0% (w/v) up to 20% (w/v); in certain embodiments, the concentration of heteropoly acid (or heteropoly anion) applied to tissue falls in the range of 1.0% (w/v) up to 10% (w/v).

In accordance with certain embodiments of the present invention, the heteropoly acid or salt thereof is applied to said tissue as a suspension.

In accordance with certain additional embodiments of the present invention, the heteropoly acid or salt thereof is applied to said tissue as a solid.

In accordance with certain embodiments of the present invention, the heteropoly acid or salt thereof is converted into the reduced form thereof by treatment with an effective amount of a suitable reducing agent.

Suitable reducing agents contemplated for use herein include materials that lead to a portion of the molybdenum, tungsten, or vanadium ions in the heteropoly acid or heteropoly anion being converted to a lower oxidation state, but that in doing so, do not irreversibly cause damage to the tissue structure or matter contained within.

Exemplary reducing agents include titanium trichloride, stannous chloride (tin(II) chloride), ascorbic acid, ascorbic acid plus potassium antimonyl tartrate, hydrazinium sulfate, 4-(methylamino)phenol sulfate, hydroquinone, 1-amino-4-naphthol-2-sulfonic acid, 2,4-diaminophenol dihydrochloride, sodium sulfite, sodium bisulfite, sodium borohydride, ferrous sulfate, ferrous ammonium sulfate, uric acid, thiourea, formamidine sulfinic acid, antimony(III) compounds, tin(II) compounds, iron(II) compounds, copper(I) compounds, sodium cyanoborohydride, and the like, as well as mixtures of any two or more thereof.

Alternatively, a suitable reducing strategy contemplated for use herein includes exposure to electromagnetic radiation of suitable frequency to promote the desired reduction. This would usually involve visible or uv radiation, optionally with sensitizer molecules. Such methodologies are well-known in the art—see, for example, Roundhill, D. M. (1994). *Photochemistry and Photophysics of Metal Complexes*. Springer, and Ferraudi, G. J. (1988). *Elements of Inorganic Photochemistry*. Wiley-Interscience, the entire contents of each of which are hereby incorporated by reference herein.

In accordance with certain embodiments of the present invention, the above-described methods further comprise conducting an immunofluorescence assay of said tissue sample before, during or after application of said heteropoly acid or salt thereof thereto.

In accordance with certain embodiments of the present invention, there are provided methods for lowering/reducing/masking/suppressing tissue autofluorescence in an immunofluorescence assay, said method comprising applying a reduced form of a heteropoly acid or salt thereof to said tissue before, during or after conducting said immunofluorescence assay.

In accordance with certain embodiments of the present invention, there are provided methods for distinguishing between:
  the signals in an immunofluorescence assay of a tissue sample due to fluorescent antibodies or probes, and
  general background tissue autofluorescence,
said methods comprising treating said tissue with a reduced form of a heteropoly acid or salt thereof, thereby suppressing tissue autofluorescence without substantially affecting the signals in said immunofluorescence assay.

In accordance with certain embodiments of the present invention, there are provided methods for the reduction of fluorescence in immunofluorescence assays of a tissue sample due to:
  aldehyde fixation,
  the presence of collagen,
  the presence of elastin, and/or
  the presence of red blood cells,
said methods comprising treating said tissue with a reduced form of a heteropoly acid or salt thereof, thereby reducing tissue autofluorescence due to aldehyde fixation, the presence of collagen, the presence of elastin, and/or the presence of red blood cells.

In accordance with certain embodiments of the present invention, there are provided kits comprising:
  a vessel containing an amount of an autofluorescence quenching agent effective for lowering/reducing/masking/suppressing tissue autofluorescence in an immunofluorescence assay, and
  a package insert with instructions for the use thereof,
wherein said quenching agent comprises a reduced form of a heteropoly acid or salt thereof.

Kits contemplated herein optionally further comprise:
  a vessel containing an effective amount of means for converting said heteropoly acid or salt thereof into the reduced form thereof.

In accordance with additional embodiments of the present invention, there are provided autofluorescence quenching agents comprising a reduced form of a heteropoly acid or salt thereof.

Various aspects of the present invention are illustrated by the following non-limiting examples. The examples are for illustrative purposes and are not a limitation on any practice of the present invention. It will be understood that variations and modifications can be made without departing from the spirit and scope of the invention.

One of ordinary skill in the art readily knows how to synthesize or commercially obtain the reagents and components described herein.

EXAMPLES

The invention will now be described in greater detail with reference to the following non-limiting examples.

Example 1

Sample Preparation

Human kidney tissue that had been formalin-fixed and paraffin embedded was sectioned into 5 micron thick sections using a microtome and affixed to slides that were pretreated with a tissue-adhesive solution (Vectabond™—Vector Laboratories, Inc. Burlingame, Calif. USA). These slides were then deparaffinized with xylene using standard methods and rehydrated. The slides were then treated with an antigen retrieval solution (Antigen Unmasking Solution, Citric Acid Based—Vector Laboratories, Inc., Burlingame, Calif. USA) according to the manufacturer's instructions, and finally stored in phosphate buffered saline (PBS), pH 7.4.

Example 2

Reagent Preparation

A series of reagents was prepared as follows:
Reagent 1—1% (w/v) phosphomolybdic acid—was prepared by dissolving 100 mg of phosphomolybdic acid hydrate (TCI Chemicals, product number P1910) in 10 mL of deionized water.
Reagent 2—1% (w/v) silicomolybdic acid—was prepared by diluting 500 μL of silicomolybdic acid solution (18.0-22.0%, Sigma Aldrich, product number 708348) with 9.5 mL of deionized water.
Reagent 3—10% (w/v) phosphotungstic acid was used as received (Sigma Aldrich, product number HT152).
Reagent 4—10% (w/v) silicotungstic acid was prepared by dissolving 400 mg of tungstosilicic acid hydrate (Sigma Aldrich, T2786) in 4 mL of deionized water.
Reagent 5—5 mg/mL tin chloride solution—was prepared by dissolving 50 mg of tin(II) chloride dihydrate (Sigma Aldrich, product number 243523) in 10 mL of 0.1 N hydrochloric acid.
Reagent 6—2.5 mg/mL sodium cyanoborohydride was prepared by dissolving 25 mg of sodium cyanoborohydride (Sigma Aldrich, product number 156159) in 10 mL of phosphate buffered saline, pH 7.4.
Summarizing the above, Reagents 1, 2, 3 and 4 are solutions of four different heteropolyacids:

Reagents 1 and 2 contain molybdenum in the +6 oxidation state (which can be reduced), and Reagents 3 and 4 contain tungsten in the +6 oxidation state (which can be reduced).

After exposure of the tissue to Reagent 1 or 2, Reagent 5 is used to lower the oxidation state of the bound molybdenum; and after exposure of the tissue to Reagent 3 or 4, Reagent 6 is used to lower the oxidation state of the bound tungsten.

Example 3

Sample Treatment

The slides prepared as described in Example 1 were assayed as follows:

Example 3A (Reagent 1/Reagent 5)

The slides were briefly washed with deionized water, placed horizontally, and Reagent 1 was added dropwise to completely cover the tissue sections. The sections were allowed to stand for 15 minutes. The sections were then briefly rinsed with deionized water, placed horizontally, and Reagent 5 was added dropwise to completely cover the tissue sections. The sections were allowed to stand for 5 minutes, rinsed with deionized water, and one drop of PBS/glycerol (1:9) added as a mounting medium. A cover slip was placed on top of the PBS/glycerol and the samples viewed under a standard epifluorescent microscope with a metal-halide lamp (Nikon).

Example 3B (Reagent 2/Reagent 5)

The slides were briefly washed with deionized water, placed horizontally, and Reagent 2 was added dropwise to completely cover the tissue sections. The sections were allowed to stand for 15 minutes. The sections were then briefly rinsed with deionized water, placed horizontally, and Reagent 5 was added dropwise to completely cover the tissue sections. The sections were allowed to stand for 5 minutes, rinsed with deionized water, and one drop of PBS/glycerol (1:9) added as a mounting medium. A cover slip was placed on top of the PBS/glycerol and the samples viewed under a standard epifluorescent microscope with a metal-halide lamp (Nikon).

Example 3C (Reagent 3/Reagent 6)

The slides were briefly washed with deionized water, placed horizontally, and Reagent 3 was added dropwise to completely cover the tissue sections. The sections were allowed to stand for 15 minutes. The sections were then briefly rinsed with deionized water, placed horizontally, and Reagent 6 was added dropwise to completely cover the tissue sections. The sections were allowed to stand for 5 minutes, rinsed with deionized water, and one drop of PBS/glycerol (1:9) added as a mounting medium. A cover slip was placed on top of the PBS/glycerol and the samples viewed under a standard epifluorescent microscope with a metal-halide lamp (Nikon).

Example 3D (Reagent 4/Reagent 6)

The slides were briefly washed with deionized water, placed horizontally, and Reagent 4 was added dropwise to completely cover the tissue sections. The sections were allowed to stand for 15 minutes. The sections were then briefly rinsed with deionized water, placed horizontally, and Reagent 6 was added dropwise to completely cover the tissue sections. The sections were allowed to stand for 5 minutes, rinsed with deionized water, and one drop of PBS/glycerol (1:9) added as a mounting medium. A cover slip was placed on top of the PBS/glycerol and the samples viewed under a standard epifluorescent microscope with a metal-halide lamp (Nikon).

Images of the autofluorescence of the tissue prior to treatment and after treatment indicate that each of the four procedures described in this example can have varying effects on the background autofluorescence of the tissue. The percentage of quenching is reported in Table 1 (as estimated by visual examination of the images).

TABLE 1

Amount of Autofluorescence Quenching Observed At 30x Magnification of Human Kidney Tissue Sections Using Green Excitation Filter Cube

| Example # (Treatment) | Autofluorescence Quenching |
|---|---|
| Example 3A (Reagent 1/Reagent 5) | >90% |
| Example 3B (Reagent 2/Reagent 5) | >90% |
| Example 3C (Reagent 3/Reagent 6) | approximately 50% |
| Example 3D (Reagent 4/Reagent 6) | approximately 30% |

The maximum effect is observed with the combination of Reagent 1/Reagent 5 (>90% quenching) or Reagent 2/Reagent 5 (>90% quenching) treatments. Reagent 3/Reagent 6 and Reagent 4/Reagent 6 treatments have less quenching observed under these conditions. Nonetheless, it is clear that using four different heteropolyacids (Reagents 1, 2, 3, 4) followed by two different reducing agents (Reagents 5, 6), autofluorescence quenching was observed in all cases with these human kidney sections.

Example 4

Additional Sample Treatment

Further experiments were conducted with six different human tissue sections.

Tissue samples were formalin-fixed and paraffin embedded and were sectioned into 5 micron thick sections using a microtome and affixed to slides that were pretreated with a tissue-adhesive solution (Vectabond™—Vector Laboratories, Inc. Burlingame, Calif. USA). These slides were then deparaffinized with xylene using standard methods and rehydrated. The slides were then treated with an antigen retrieval solution (Antigen Unmasking Solution, Citric Acid Based—Vector Laboratories, Inc., Burlingame, Calif. USA) according to the manufacturer's instructions, and finally stored in phosphate buffered saline (PBS), pH 7.4.

Each of the six tissue sections were treated with the Reagent 1/Reagent 5 combination, and the results of the autofluorescence quenching are presented in Table 2.

TABLE 2

Amount of Autofluorescence Quenching Observed At 30x Magnification of Different Human Tissue Sections Using Green Excitation Filter Cube using Reagent 1/Reagent 5 Treatment

| Tissue type | Autofluorescence Quenching |
| --- | --- |
| prostate | ~80% |
| colon | ~80% |
| pancreas | >90% |
| skin | ~80% |
| thymus | ~80% |
| placenta | >90% |

Invention methods are seen to dramatically reduce autofluorescnce in a variety of tissue types.

Example 5

Additional Sample Treatment

Further experiments were conducted with different concentrations of phosphomolybdic acid to determine the effects of concentration of the heteropolyacid on lowering the autofluorescence of kidney tissue. These tissue samples were formalin-fixed and paraffin embedded and were sectioned into 5 micron thick sections using a microtome and affixed to slides that were pretreated with a tissue-adhesive solution (Vectabond™—Vector Laboratories, Inc. Burlingame, Calif. USA). These slides were then deparaffinized with xylene using standard methods and rehydrated. The slides were then treated with an antigen retrieval solution (Antigen Unmasking Solution, Citric Acid Based—Vector Laboratories, Inc., Burlingame, Calif. USA) according to the manufacturer's instructions, and finally stored in phosphate buffered saline (PBS), pH 7.4.

Reagent 1 was diluted with 0.01 N HCl to the following concentrations:

0.1%, 0.01%, 0.005%, 0.0025%, 0.002%, 0.001%, and 0.0005%.

The kidney sections were treated with these seven solutions as described above, and then treated with Reagent 5 as described above. The results of the autofluorescence quenching are presented in Table 3.

To test the upper end of concentrations suitable for use with phosphomolybdic acid, solid crystals of phosphomolybdic acid hydrate were applied to kidney sections in place of Reagent 1 as described above. Since the tissue was still somewhat hydrated, the phosphomolybdic acid crystals dissolved and bound to the tissue in the vicinity where the crystals were deposited. The tissue was then treated with Reagent 5 as described above, and the results of the quenching are presented in Table 3.

To further test the upper end of concentrations suitable for use with phosphomolybdic acid, a saturated solution of phosphomolybdic acid hydrate in water (74%) was applied to kidney sections in place of Reagent 1 as described above. The tissue was then treated with Reagent 5 as described above, and the results of the quenching are presented in Table 3.

TABLE 3

Amount of Autofluorescence Quenching Observed At 30x Magnification of Human Kidney Tissue Sections Using Green Excitation Filter Cube using different concentrations of phosphomolybdic acid, followed by Reagent 5.

| Phosphomolybdic Acid Concentration | Autofluorescence Quenching |
| --- | --- |
| 0.1% | >90% |
| 0.01% | approximately 90% |
| 0.005% | approximately 70% |
| 0.0025% | approximately 30-50% |
| 0.002% | approximately 10-20% |
| 0.001% | 0% |
| 0.0005% | 0% |
| solid crystals | >90% in vicinity of crystals |
| saturated solution (74%) | >90% |

Invention methods are seen to dramatically reduce autofluorescnce at a variety of concentrations.

Various modifications of the present invention, in addition to those shown and described herein, will be apparent to those skilled in the art of the above description. Such modifications are also intended to fall within the scope of the appended claims.

Publications mentioned in the specification are indicative of the levels of those skilled in the art to which the invention pertains. These publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

That which is claimed is:

1. A method for lowering/reducing/masking/suppressing tissue autofluorescence in an immunofluorescence assay, said method comprising, before or during conducting said immunofluorescence assay:
   providing a tissue comprising lung, liver, heart, nervous system, skin, lymph gland, musculoskeletal, spleen, eye, sinus, nasal mucosa, larynx, gastrointestinal tract tissue, reproductive organ, breast, prostate, salivary gland, tonsil, or kidney tissue;
   applying a heteropoly acid or salt thereof to said tissue, wherein the heteropoly acid comprises phosphomolybdic acid, phosphotungstic acid, silicomolybdic acid, silicotungstic acid, or a mixture of any two or more thereof or salts thereof;
   reducing at least a portion of said heteropoly acid or salt thereof to a reduced form with a reducing agent; and
   measuring the immunofluorescence of the tissue.

2. The method of claim 1 wherein the reducing agent comprises an ascorbic acid or salts thereof.

3. The method of claim 1 wherein said heteropoly acid or salt thereof is applied to said tissue before measuring the fluorescence of the tissue.

4. The method of claim 3 wherein said heteropoly acid or salt is applied to said tissue before the reducing step.

5. The method of claim 3 wherein said heteropoly acid or salt thereof is applied to said tissue in reduced form.

6. The method of claim 1 wherein said heteropoly acid or salt thereof is applied to said tissue while conducting said immunofluorescence assay.

7. The method of claim 6 wherein said heteropoly acid or salt thereof is subsequently reduced.

8. The method of claim 6 wherein said heteropoly acid or salt thereof is applied in reduced form.

9. The method of claim 1 wherein when the heteropoly acid is applied in salt form, the salt comprises a counter-ion for said heteropoly anion which is a monovalent metal ion; a divalent metal ion; a trivalent metal ion; a quaternary ammonium cation; a quaternary phosphonium cation; or a mixture of any two or more thereof.

10. The method of claim 1 wherein said heteropoly acid or salt thereof is applied to said tissue as a solution.

11. The method according to claim 10 wherein said heteropoly acid or heteropoly anion is applied as a solution in a range of concentrations from 0.002% (w/v) up to a saturated solution.

12. The method of claim 1 wherein said heteropoly acid or salt thereof is applied to said tissue as a suspension.

13. The method of claim 1 wherein said heteropoly acid or salt thereof is applied to said tissue as a solid.

14. The method of claim 1 wherein said heteropoly acid or salt thereof binds to hydrophilic regions of the tissue.

\* \* \* \* \*